United States Patent [19]

Derouane et al.

[11] Patent Number: 4,652,684

[45] Date of Patent: Mar. 24, 1987

[54] VANILLIN EXTRACTION PROCESS USING LARGE PORE, HIGH SILICA/ALUMINA RATIO ZEOLITES

[75] Inventors: Eric G. Derouane, Namur, Belgium; Ralph A. Powell, Hopewell, N.J.

[73] Assignee: Mobil Oil Corporation, New York, N.Y.

[21] Appl. No.: 794,875

[22] Filed: Nov. 4, 1985

[51] Int. Cl.$^4$ .................. C07C 47/58; C07C 45/90
[52] U.S. Cl. .................................................. 568/438
[58] Field of Search ........................................ 568/438

[56] References Cited

U.S. PATENT DOCUMENTS

| | | | |
|---|---|---|---|
| 2,449,364 | 9/1948 | Blankart | 568/438 |
| 2,897,238 | 7/1959 | Toppel | 568/438 |
| 4,016,180 | 4/1977 | Baierl | 568/438 X |
| 4,277,626 | 7/1981 | Forss et al. | 568/438 |

*Primary Examiner*—Bernard Helfin
*Attorney, Agent, or Firm*—Alexander J. McKillop; Michael G. Gilman; Howard M. Flournoy

[57] ABSTRACT

A spent lignin fermented waste-liquor solution containing vanillin is treated to remove the vanillin by contacting it with a suitable large pore zeolite.

10 Claims, No Drawings

VANILLIN EXTRACTION PROCESS USING LARGE PORE, HIGH SILICA/ALUMINA RATIO ZEOLITES

BACKGROUND OF THE INVENTION

The present invention relates to the extraction of vanillin from lignin fermented spent waste liquors using large pore, high silica/alumina ratio zeolite. More particularly the vanillin is extracted from fermented spent waste liquors by contacting these liquors with large pore, high silica/alumina ratio zeolites such as Beta, ZSM-20 or dealuminated Zeolite Y.

In spite of the well known properties of zeolites as a general class of adsorbents they have not heretofore been found suitable selective adsorbents for vanillin. More particularly, few of the known molecular sieve zeolites have pores large enough to admit molecules the size of vanillin and those that do, such as Zeolite X and Zeolite Y for instance, have a greater selectivity towards the molecules in the extract which are more polar than vanillin.

DISCUSSION OF PRIOR ART

Vanillin is a common name for 3-methoxy-4-hydroxybenzaldehyde. It occurs in nature as a glucoside which hydrolyzes to vanillin and sugar. It has been identified in many oils, balsams, resins, and woods. The best known natural source is the vanillin plant, a member of the orchid family. The vanillin bean was used by the Mexican Indians at the time of the Spanish Conquest and was brought to Europe at the beginning of the 16th century. Since then it has been a favorite food flavor. Besides being a very popular flavor in the food industry it is also useful in the synthesis of drugs; 40% of the vanillin produced is consumed in manufactured drugs such as Aldomet, L-dopa and T-trimethaprin. Vanillin is also used in perfume and metal-plating industries. Although vanillin is obtained principally from natural sources, it is also produced synthetically, about 10 to 20% is made synthetically from quaiacol.

Today vanillin is derived principally from lignin, the main component in the spent sulfide liquors from sulfite pulp mills. The lignin processes are generally based on an alkaline air oxidation of a fermented spent-waste liquor from a sulfite pulp mill. The source of alkali is either sodium hydroxide or a combination of lime and soda ash which produces sodium hydroxide. The reactions are generally run at about 160° to about 175° C., at a pressure of about 150 to about 160 psig for about 2 hours. The reaction product is treated differently by each manufacturer to isolate and purify the vanillin.

Practical processes for the recovery of vanillin are: (1) the lignin process based on an alkali air-oxidation of a fermented spent waste liquor from a sulfite pulp mill followed by a variety of steps including among others, extraction with an organic solvent such as toluene (Ontario Paper Company); (2) a process related to (1) above where the organic solvent is 2-propanol or butanol (Monsanto, ITT); (3) a process related to (1) above where the liquor is upgraded by ultrafiltration (Borregaard), in particular to remove low molecular weight compounds that cannot be oxidized to vanillin.

It is known that caffeine can be selectively adsorbed from aqueous solutions by contacting them with the steamed low sodium form of Zeolite Y (see European Patent Application No. 13,451 assigned to Union Carbide Corporation). Removal of alkaloids by selective sorption from their aqueous solutions or extracts is disclosed in copending U.S. application Ser. No. 641,808, filed Aug. 17, 1984 and entitled "Removal of Caffeine, Theophylline and Theobromine from Aqueous Solutions by Selective Adsorption Using Zeolite Beta and Zeolite ZSM-20". Further, U.S. Pat. No. 2,491,832, describes a method of vanillin extraction from organic solutions. However, the present invention, unlike any prior art known to applicants, is directed to a novel, inexpensive method for the recovery of vanillin from lignin fermented spent waste liquors in the absence of solvent extraction and/or upgrading of the lignin liquor.

SUMMARY OF THE INVENTION

Briefly stated, this invention comprises the use of large pore, high silica/alumina ratio zeolites such as Zeolite ZSM-20, Zeolite Beta, or dealuminated Zeolite Y for removing vanillin from various liquid solutions, particularly from fermented spent waste-liquors containing vanillin. Mixtures of these zeolites can also be used.

DESCRIPTION OF THE INVENTION

The process of the present invention comprises vanillin extraction from lignin fermented spent waste-liquors by contacting these liquors with the large pore ($\gtrsim 0.7$ nm) and high $SiO_2/Al_2O_3$ ratio zeolites (10–100). These zeolites have large sorption capacities. They also have pores wide enough to admit large semi-polar molecules (vanillin has an aldehydic, a phenolic, and a methoxy group substituting a benzene ring). Such zeolites as Zeolite ZSM-20, Zeolite Beta, and dealuminated Zeolite Y can act as selective sorbents for such molecules when they have a relatively high silica/alumina ratio (about 10 to about 100 and preferably 10–35 and in some instances ratios of 4.5 to 35 may be preferred). These zeolite forms, in particular while having a low Na content, also have a rather low polarity, contrary to conventional X and Y zeolites which are hydrophilic and have more affinity for highly polar molecules.

The crystalline zeolites preferred are known in the art as "large Pore" and have a high silica to alumina mole ratio between 10–100 and more preferably 10–35 and a preponderance of pores greater than 7 angstroms in diameter. Particularly preferred zeolites are Zeolite Beta and ZSM-20. However, any suitable large pore zeolite may be used.

The composition of Zeolite ZSM-20 and its method of preparation, as well as its distinguishing x-ray diffraction pattern are disclosed in U.S. Pat. No. 3,972,983 to Ciric which is incorporated herein in its entirety by reference.

The composition of Zeolite Beta, as well as the method of its preparation is disclosed in U.S. Pat. No. 3,308,069 and RE No. 28,341 which are incorporated in their entirety herein by reference.

Zeolite Y is disclosed in U.S. Pat. No. 3,130,007 which is incorporated herein by reference. U.S. Pat. No. 4,331,694 discloses a particular form of zeolite Y, denominated UHP-Y. In general, these UHP-Y zeolites are characterized to distinguish them from other zeolites as having a silica to alumina molar ratio of from 4.5 to 35. As those skilled in the art will appreciate, the dealuminization of zeolites is a difficult and expensive procedure to follow in the industry. Zeolites which do not require such treatment would be more desirable for the adsorption of vanillin from aqueous solutions.

The method of contacting the zeolite with the waste liquors is not critical. Preferably, the zeolite adsorbent is contained in a fixed adsorption bed and the solution to be treated passed through the bed until breakthrough of vanillin occurs or is imminent. The spent liquors are contacted with the zeolites at temperatures ranging from 0° to about 100° C. under ambient pressure, although slightly higher pressures may be used if so desired. Regeneration of the adsorbent bed and recovery of the vanillin is advantageously accomplished by passing a desorbent solvent countercurrently through the bed at an elevated temperature, preferably from about 20° C. to 80° C. Any suitable solvent may be used, ethanol is preferred. It is also feasible to form a slurry of zeolite particles with the lignin fermented waste-liquor vanillin solution and then isolate the resulting loaded zeolite from the treated solution by filtration, centrifugation and the like.

Lignin is a replenishable resource. The method which is proposed is accomplished by the absence of solvent extraction and/or upgrading of the lignin liquor. Accordingly, a novel inexpensive method for the recovery of vanillin from lignin fermented spent waste liquors is hereby disclosed.

The use of dealuminated Zeolite Y, Beta, or ZSM-20 which are wide pore, large capacity, low polarity zeolites (in particular in the form having low Na content and relatively high $SiO_2/Al_2O_3$ ratio) as a selective sorbent bed acting on acidified liquors (following alkaline oxidation and acidification) offers several advantages. In particular, extraction by an organic solvent and upgrading by ultrafiltration are no longer needed. A route is thereby provided to a direct, economical, and substantially free of contaminants (which might be a health problem) for vanillin recovery.

Although the present invention has been described with preferred embodiments, it is to be understood that modifications and variations may be resorted to, without departing from the spirit and scope of this invention, as those skilled in the art will readily understand. Such modifications and variations are considered to be within the purview and scope of the appended claims.

We claim:

1. A process for removing vanillin from a solution comprising lignin fermented waste-liquor which comprises contacting said solution with a large pore, low sodium, low polarity, crystalline zeolite having a silica to alumina mole ratio between about 10–35 to 100 and a pore size $\geq 0.7$ nm under removal conditions whereby vanillin is adsorbed on said zeolite, and thereafter recovering the vanillin from said solution.

2. The process of claim 1 wherein the zeolite contacts the lignin solution at temperatures ranging from about 0° to about 100° C. and at pressures ranging from ambient.

3. The process of claim 1 wherein the zeolite is in slurry form.

4. The process of claim 3 wherein after the vanillin is adsorbed, the zeolite is isolated and the vanillin recovered therefrom.

5. A process for removing vanillin from an aqueous solution of lignin fermented spent waste liquor which comprises contacting said aqueous solution with a zeolite selected from the group consisting of dealuminated Zeolite Y, Zeolite Beta and Zeolite ZSM-20 whereby said vanillin is adsorbed on said zeolite, and thereafter recovering said vanillin from said zeolite.

6. The process of claim 5 wherein the zeolite contacts the lignin solution at temperatures ranging from about 0° to about 100° C. at ambient pressures.

7. The process of claim 5 wherein the zeolite in slurry form.

8. The process of claim 7 wherein after said contacting the zeolite is isolated and the vanillin removed therefrom.

9. The process of claim 5 wherein the adsorbed vanillin is desorbed from the zeolite by contacting said zeolite with a suitable solvent at a temperature of at least about 20° C.

10. The process of claim 9 wherein said solvent is ethanol.

* * * * *